United States Patent
Thompson et al.

(10) Patent No.: US 12,257,455 B2
(45) Date of Patent: Mar. 25, 2025

(54) VIRTUAL PORTAL IMAGE FOR TREATMENT SETUP IN A RADIATION THERAPY SYSTEM

(71) Applicant: SIEMENS HEALTHINEERS INTERNATIONAL AG, Steinhausen (CH)

(72) Inventors: Stephen Thompson, Pacific Grove, CA (US); Andres Graf, Oberwil (CH); Susan Koehl, Henderson, NV (US)

(73) Assignee: SIEMENS HEALTHINEERS INTERNATIONAL AG (CH)

( * ) Notice: Subject to any disclaimer, the term of this patent is extended or adjusted under 35 U.S.C. 154(b) by 258 days.

(21) Appl. No.: 17/958,292

(22) Filed: Sep. 30, 2022

(65) Prior Publication Data

US 2024/0108915 A1 Apr. 4, 2024

(51) Int. Cl.
*A61N 5/10* (2006.01)

(52) U.S. Cl.
CPC ......... *A61N 5/1039* (2013.01); *A61N 5/1049* (2013.01); *A61N 2005/1062* (2013.01)

(58) Field of Classification Search
CPC ........ A61N 5/10; A61N 5/1001; A61N 5/103; A61N 5/1031; A61N 5/1039; A61N 5/1049; A61N 5/107; A61N 2005/1056; A61N 2005/1062; A61N 2005/1092; A61N 2005/1097; A61B 6/032; A61B 6/4085; G16H 20/40
See application file for complete search history.

(56) References Cited

U.S. PATENT DOCUMENTS

| | | |
|---|---|---|
| 6,466,813 B1 | 10/2002 | Shukla et al. |
| 2005/0080332 A1 | 4/2005 | Leber et al. |
| 2008/0031406 A1 | 2/2008 | Martinez et al. |
| 2010/0067660 A1 | 3/2010 | Core et al. |
| 2010/0119032 A1 | 5/2010 | Yan et al. |
| 2013/0188856 A1 | 7/2013 | Adler, Jr. et al. |

(Continued)

FOREIGN PATENT DOCUMENTS

| | | |
|---|---|---|
| CN | 102233158 B | 7/2014 |
| CN | 107358607 A | 11/2017 |

(Continued)

OTHER PUBLICATIONS

The Extended European Search Report, Application No. 18214849.4, Jun. 18, 2019.

(Continued)

*Primary Examiner* — Jurie Yun
(74) *Attorney, Agent, or Firm* — SU IP CONSULTING

(57) ABSTRACT

A computer-implemented method of performing radiation therapy on a target volume within an anatomical region of a patient includes: acquiring a cone-beam computed tomography (CBCT) image of the region while the region is positioned in a first preliminary treatment location; reconstructing a current digital volume of the region based on the CBCT image of the region; generating a first beam's-eye-view of the region based on the current digital volume and an offset between the first preliminary treatment location and a reference treatment location; modifying the first beam's-eye-view of the region with one or more visual cues associated with a treatment field for the target volume; and displaying the first beam's-eye-view with the one or more visual cues.

20 Claims, 10 Drawing Sheets

(56) References Cited

U.S. PATENT DOCUMENTS

| | | |
|---|---|---|
| 2014/0046212 A1 | 2/2014 | Deutschmann |
| 2015/0290473 A1 | 10/2015 | Abdul-Hamid et al. |
| 2016/0114192 A1 | 4/2016 | Lachaine et al. |
| 2016/0175617 A1 | 6/2016 | Spatola et al. |
| 2016/0175671 A1 | 6/2016 | Schmidt |
| 2017/0189717 A1 | 7/2017 | MacDonald et al. |
| 2017/0361128 A1 | 12/2017 | Lachaine et al. |
| 2019/0192881 A1 | 6/2019 | Thieme-Marti et al. |

FOREIGN PATENT DOCUMENTS

| | | |
|---|---|---|
| CN | 105342631 B | 1/2019 |
| EP | 3106093 B1 | 5/2019 |
| JP | 2001340474 A | 12/2001 |

OTHER PUBLICATIONS

The Extended European Search Report, Application No. 20200690.4, Mar. 9, 2021.
Yawei Zhang et al., "Reducing Scan Angle Using Adaptive Prior Knowledge for a Limited-Angle Intrafraction Verification (LIVE) System for Conformal ARC Radiotherapy", Physics in Medicine & Biology, 2017, pp. 3859-3882, vol. 62.
Lei Ren et al., "A Limited-Angle Intrafraction Verification (LIVE) System for Radiation Therapy", Medical Physics Letter, Feb. 2014, vol. 31, No. 2.

VIRTUAL PORTAL IMAGE FOR TREATMENT SETUP IN A RADIATION THERAPY SYSTEM

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area. For example, a treatment planning scan is often performed via computed tomography (CT) to generate the three-dimensional image. From such imaging, the size and mass of the target tissue can be estimated, a planning target volume determined, and an appropriate treatment plan generated.

So that the prescribed dose is correctly supplied to the planning target volume during radiation therapy, a patient must be correctly positioned relative to the linear accelerator that provides the radiation therapy. To that end, X-ray imaging of the anatomical region surrounding the planning target volume is commonly performed immediately prior to the delivery of an X-ray treatment beam. For instance, for many breast cancer treatments, portal imaging is performed to verify patient positioning and target localization. Generally, in conventional radiation therapy systems, a portal image (also referred to as a "port film") is acquired with a therapeutic megavoltage (MV) beam, and indicates whether the planned treatment field intersects with too much of the lung and/or extends a required distance beyond the skin of the patient (the "flash distance"). Because portal images are acquired along a beam's-eye view of the therapeutic MV beam, flash distance and heart/lung sparing can be readily measured with a single portal image for each planned therapeutic beam by a radiation therapist or physician at the time of treatment.

For the implementation of image-guided radiation therapy (IGRT), radiation therapy systems have been developed that include on-board imaging, such as kilovolt cone-beam computed tomography (kV-CBCT) imaging systems. Such on-board imaging systems can be used in lieu of MV portal imaging to verify patient positioning and target localization, and with a greatly reduced dose. Further, an on-board CBCT imaging system acquires images that enable the reconstruction of a three-dimensional volume of patient anatomy, which can provide a wealth of visual information related to a planning target volume, the associated treatment field, and any three-dimensional translations needed to fine-tune patient position. One drawback to CBCT on-board imaging systems is that users who are accustomed to verifying flash distance and heart/lung sparing via conventional portal images can be hesitant or even unable to assess the appropriateness of a particular radiation therapy treatment field based on a three-dimensional CBCT reconstruction. As a result, visualization and analysis of a radiation therapy treatment field by such a user can take significantly longer than when a conventional portal image is used. Worse, in some instances the visualization capabilities of the on-board CBCT imaging system are not fully utilized, and instead a conventional portal image may be acquired for verifying flash distance and heart/lung sparing.

Accordingly, there is a need in the art for techniques to facilitate treatment setup in a radiation therapy system.

SUMMARY

In accordance with at least some embodiments, a cone-beam computed tomography (CBCT) imaging system of a radiation therapy system is configured to generate a virtual portal image of an anatomical region of a patient based on volume data that are acquired while the patient is disposed in a preliminary treatment location. For example, CBCT image data of the anatomical region may be acquired immediately prior to delivery of treatment and a digital volume of the anatomical region reconstructed from the CBCT image data. The virtual portal image is then generated based on the digital volume. In the embodiments, the virtual portal image enables a radiation therapist, physician, or other user to verify patient positioning and target localization relative to a planned treatment field without acquiring and analyzing a traditional portal image (also referred to as a "port film"). In some embodiments, the virtual portal image can be image processed to visually mimic the appearance of a traditional portal image, and can include one or more visual cues associated with the treatment field, such as a field outline and/or a graticule or other graduated visual indicator of positions within the treatment field. With the inclusion of visual cues like the field outline and graticule, a user can readily determine flash distance and/or sparing of organs at risk, even when the user is accustomed to analyzing traditional portal images.

In accordance with at least some embodiments, a computer-implemented method for a radiation therapy system includes: acquiring a cone-beam computed tomography (CBCT) image of the region while the region is positioned in a first preliminary treatment location; reconstructing a current digital volume of the region based on the CBCT image of the region; generating a first beam's-eye-view of the region based on the current digital volume and an offset between the first preliminary treatment location and a reference treatment location; modifying the first beam's-eye-view of the region with one or more visual cues associated with a treatment field for the target volume; and displaying the first beam's-eye-view with the one or more visual cues.

In accordance with at least some embodiments, a radiation therapy system includes: an imaging X-ray source configured to rotate about an isocenter of the radiation treatment system and direct imaging X-rays to a target region that includes a target volume and a processor. In the embodiments, the processor is configured to perform the steps: acquiring a cone-beam computed tomography (CBCT) image of the region while the region is positioned in a first preliminary treatment location; reconstructing a current digital volume of the region based on the CBCT image of the region; generating a first beam's-eye-view of the region based on the current digital volume and an offset between the first preliminary treatment location and a reference treatment location; modifying the first beam's-eye-view of the region with one or more visual cues associated with a treatment field for the target volume; and displaying the first beam's-eye-view with the one or more visual cues.

Further embodiments include a non-transitory computer-readable storage medium comprising instructions that cause a computer system to carry out one or more of the above methods, as well as a computer system configured to carry out one or more of the above methods.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
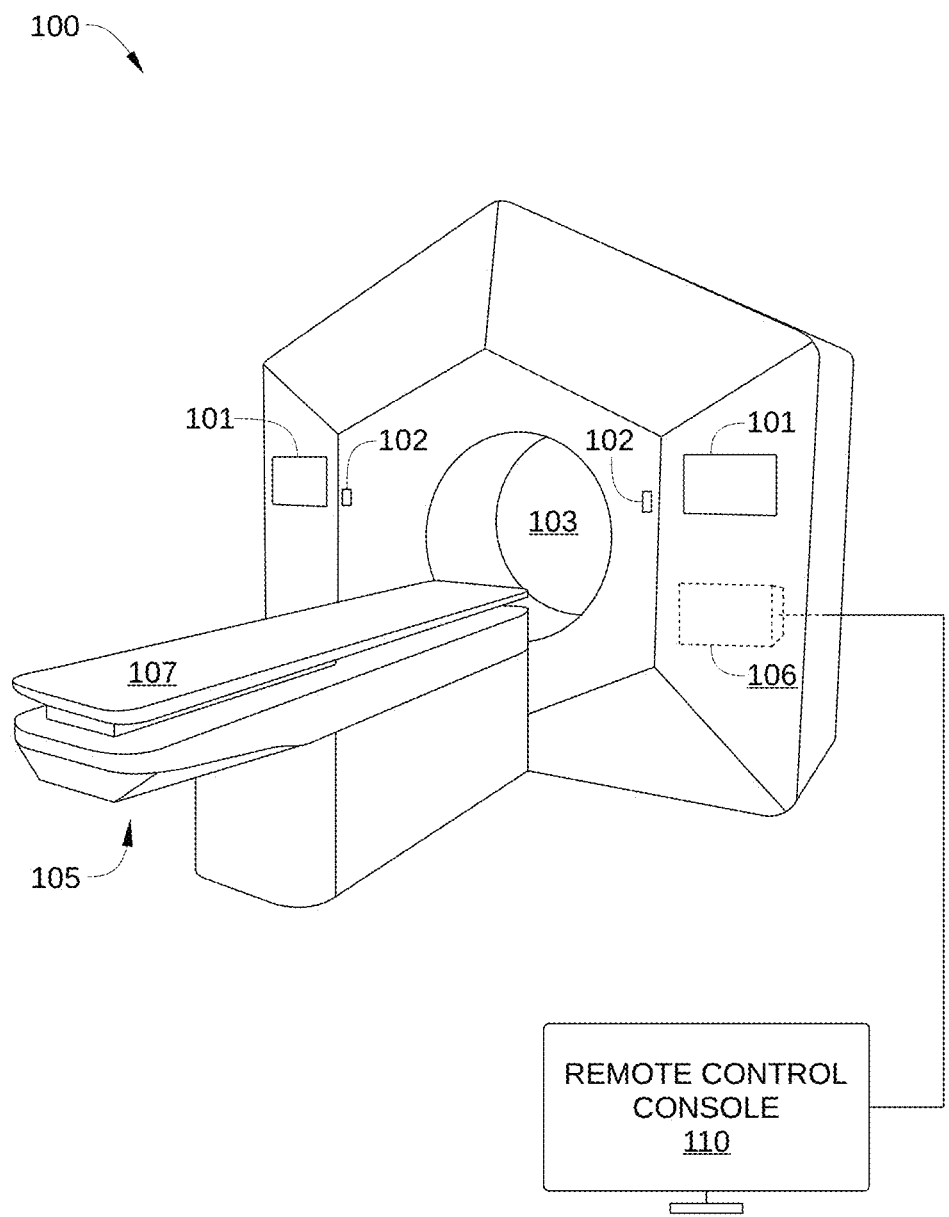
FIG. 1 is a perspective view of a radiation therapy system, according to various embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

System Overview

FIG. 1 is a perspective view of a radiation therapy (RT) system 100, according to various embodiments. RT system 100 is configured to image patient anatomy surrounding a planning target volume, such as a tumor, and reconstruct a digital volume of the patient anatomy that includes the planning target volume. In some embodiments, radiation therapy system 100 performs such imaging via a cone-beam computed tomography (CBCT) process using one or more imagers incorporated in radiation therapy system 100, such as one or more kilovolt (kV) X-ray imagers. In some embodiments, RT system 100 is a radiation system configured to detect inter-fraction motion using X-ray imaging techniques. In some embodiments, RT system 100 is a radiation system configured to detect intra-fraction motion in near-real time using X-ray imaging techniques. Thus, in such embodiments, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, RT system 100 is described herein configured with a circular gantry. In other embodiments, RT system 100 can be configured with a C-gantry capable of infinite rotation via a slip ring connection.

Generally, RT system 100 is capable of kV imaging of a target volume, to generate treatment planning image information (such as a treatment planning scan) and/or to generate images during a radiation therapy treatment fraction. Thus, in some embodiments, RT system 100 can be employed in addition to or instead of a treatment planning computed tomography imager. Further, in some embodiments, RT system is configured to image a target volume immediately prior to and/or during application of an MV treatment beam, so that an image-guided radiation therapy (IGRT) process and/or an intensity-modulated radiation therapy (IMRT) process can be performed using X-ray imaging. RT system 100 may include one or more touch-screens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location.

Figure 2:
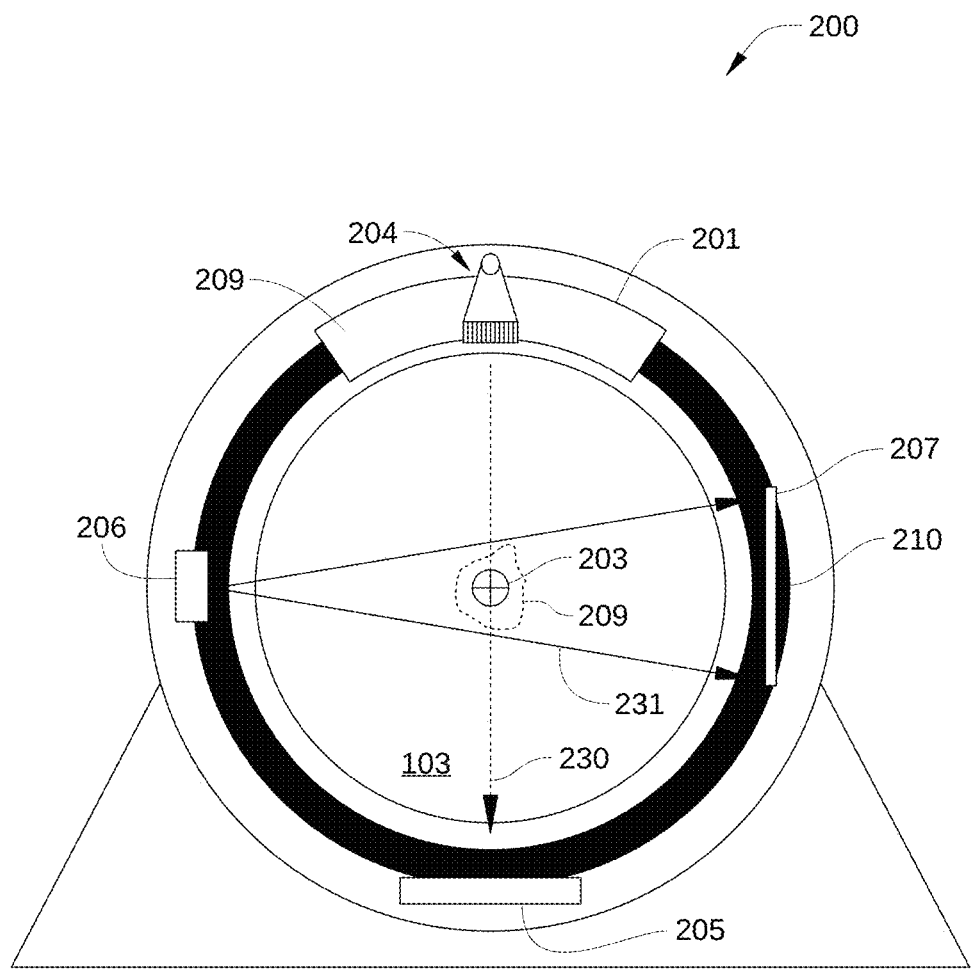
FIG. 2 schematically illustrates a drive stand and gantry of the radiation therapy system of FIG. 2, according to various embodiments.

FIG. 2 schematically illustrates a drive stand 200 and gantry 210 of RT system 100, according to various embodiments. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT system 100, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT system 100, gantry 220 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates a MV treatment beam 230 of high energy X-rays (or in some embodiments electrons, protons, and/or other heavy charged particles, ultrahigh dose rate X-rays (e.g., for FLASH radiotherapy) or microbeams for microbeam radiation therapy) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In some embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can be generated. In some embodiments, CBCT can be employed to generate treatment planning images. Additionally or alternatively, in some embodiments, CBCT is employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape. Alternatively, or additionally, in some embodiments, partial-data reconstruction is performed by RT system 100 during portions of an IGRT or IMRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. One such embodiment is illustrated in FIG. 3.

Figure 3:
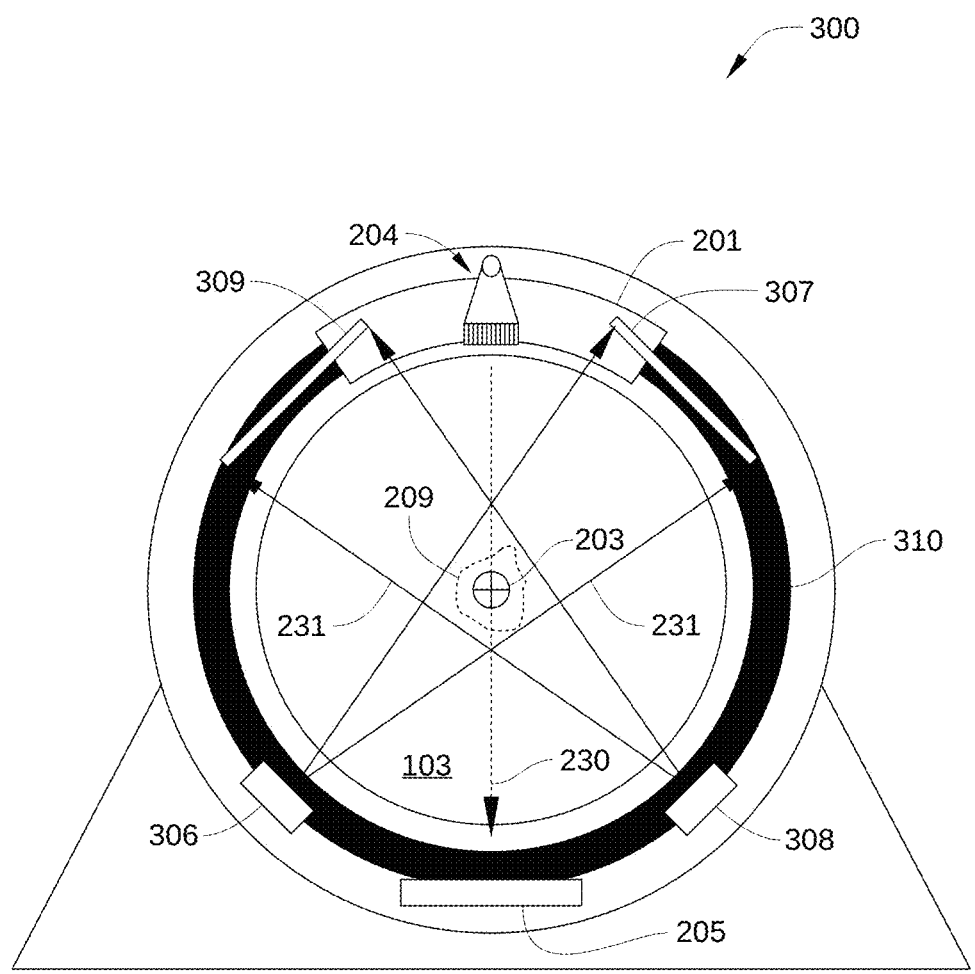
FIG. 3 schematically illustrates a drive stand and a gantry of the radiation therapy system of FIG. 2, according to various embodiments.

FIG. 3 schematically illustrates a drive stand 300 and gantry 310 of RT system 100, according to various embodiments. Drive stand 300 and gantry 310 are substantially similar in configuration to drive stand 200 and gantry 210 in FIG. 2, except that the components of RT system 100 that are mounted on gantry 310 include a first imaging X-ray source 306, a first X-ray imager 307, a second imaging X-ray source 308, and a second X-ray imager 309. In such embodiments, the inclusion of multiple X-ray imagers in RT system 100 facilitates the generation of projection images (for reconstructing the target volume) over a shorter image acquisition arc. For instance, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 207 (or by first x-ray imager 307 and second X-ray imager 309) are used to construct imaging data for a digital volume of patient anatomy within a 3D region that includes the target volume. Alternatively or additionally, such projection images can be used to update portions of existing imaging data for the digital volume corresponding to the 3D region. One embodiment of such a digital volume is described below in conjunction with FIG. 4.

Figure 4:
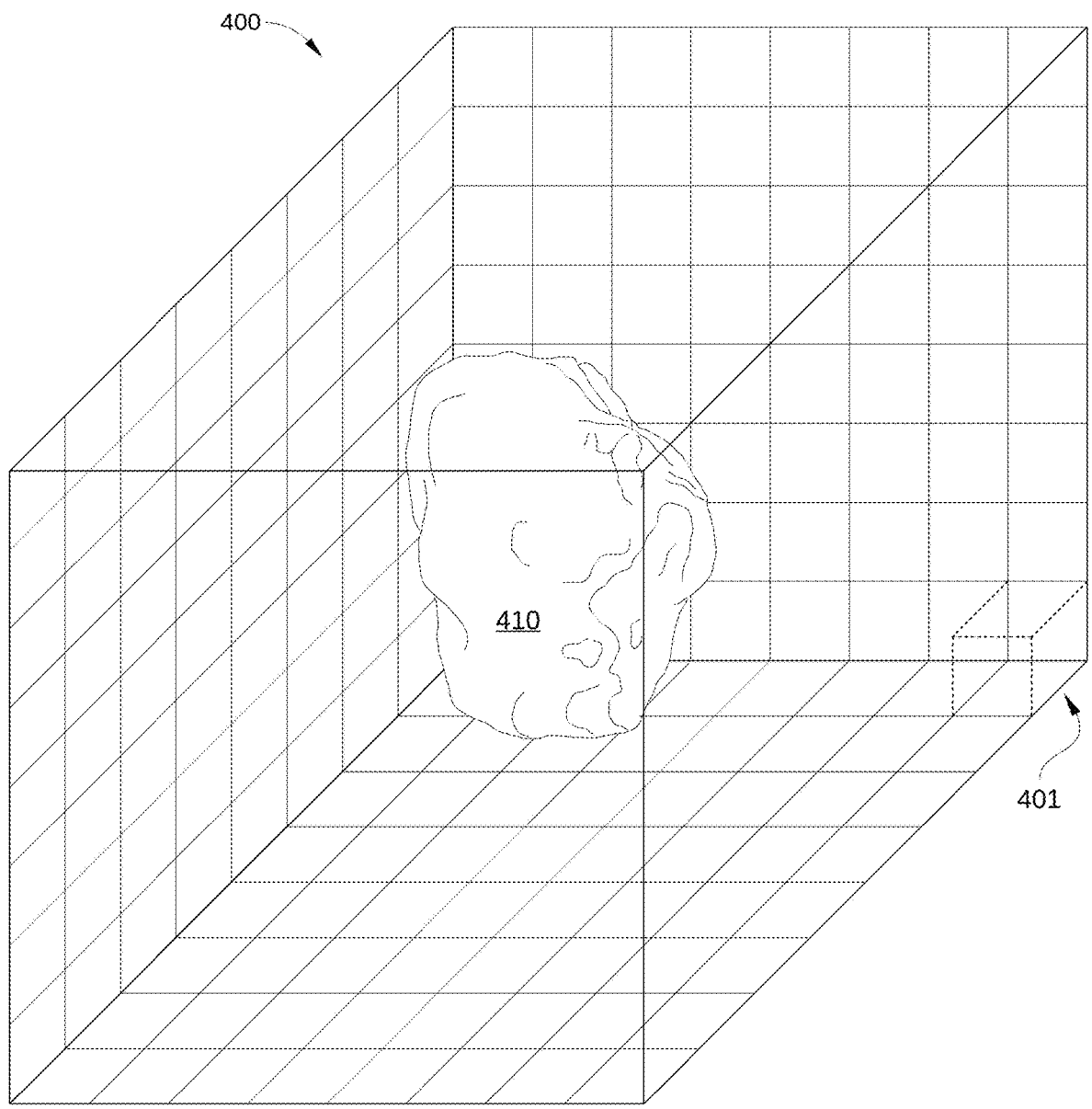
FIG. 4 schematically illustrates a digital volume that is constructed based on projection images of an anatomical region generated by one or more X-ray imagers included in the radiation therapy system of FIG. 2, according to various embodiments.

FIG. 4 schematically illustrates a digital volume 400 that is constructed based on projection images of an anatomical region generated by one or more X-ray imagers included in RT system 100, according to various embodiments. For example, in some embodiments, the projection images can be generated by a single X-ray imager, such as X-ray imager 207, and in other embodiments the projection images can be generated by multiple X-ray imagers, such as first x-ray imager 307 and second X-ray imager 309.

Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the GTV, CTV, or the PTV for a particular treatment. The GTV depicts the position and extent of the gross tumor, for example what can be seen or imaged; the CTV includes the GTV and an additional margin for sub-clinical disease spread, which is generally not imagable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 400.

According to various embodiments described below, image information associated with each voxel 401 of digital volume 400 is constructed via projection images generated by the single or multiple X-ray imagers via a CBCT process.

For example, such a CBCT process can be employed immediately prior to delivering treatment beam 230 to target volume 410, so that the location and shape of target volume 410 can be confirmed before treatment begins.

Overview of Radiation Therapy Process

Figure 5:
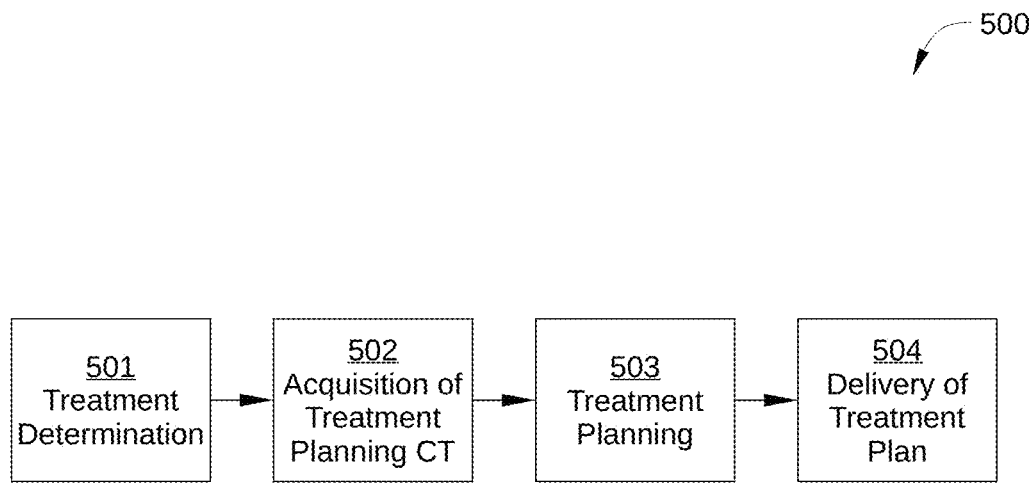
FIG. 5 is a block diagram illustrating an example radiation therapy process, according to various embodiments.

FIG. 5 is a block diagram illustrating an example radiation therapy process 500. Radiation therapy process 500 includes a plurality of steps 501-504 that are performed to deliver a treatment plan for a particular patient. Radiation therapy process 500 is performed in response to a diagnosis for a patient that indicates the patient is to be treated via external beam radiation therapy. The diagnosis typically indicates external beam radiation therapy based on various factors, including: the type of cancer tumor that has been detected, the size of the detected tumor, the location of the tumor in the body, proximity of the tumor to organs at risk (OARs) or other normal tissues that are sensitive to radiation, the general health and medical history of the patient, the presence of other types of cancer in the patient, the age of the patient, certain medical conditions of the patient, and the like.

As shown, radiation therapy process 500 includes one or more of the following steps: a treatment determination step 501, an acquisition of treatment planning computerized tomography (CT) step 502, a treatment planning step 503, and a delivery of treatment plan step 504.

In treatment determination step 501, patient imaging, tumor pathology, and diagnosis for the patient is reviewed, and one or more possible treatment approaches or prescriptions for radiation therapy are determined. In some instances, step 501 is performed by a radiation oncologist, who may be employed at the clinical location where the radiation therapy will ultimately take place. In some instances, the radiation oncologist can be assisted by a software application configured to generate possible treatment approaches based on the diagnosis and imaging information for the patient. In such instances, the radiation oncologist selects and/or modifies one or more of the treatment approaches offered by the software application.

In acquisition of treatment planning CT step 502, a treatment planning CT scan is specified and performed that shows the tumor and an anatomical region around the tumor. For example, a radiation oncologist may specify some or all of the parameters of the treatment planning CT scan. Alternatively, in some instances, the radiation oncologist can be assisted by a software application configured to specify potential parameters for the treatment planning CT. In step 502, the treatment planning CT is generated by scanning the patient, for example during a clinical visit, and a treatment planning image is generated based on the images acquired as part of the treatment planning CT. This treatment planning image can be employed subsequently as a reference image of the anatomical region of interest.

In treatment planning step 503, a treatment plan is generated based on the treatment planning CT. For example, the gross tumor volume (GTV), the clinical target volume (CTV), the internal target volume (ITV), the planning target volume (PTV), OARs, and/or a planning organ at risk volume (PRV), among others, may be specified, for example via a segmentation process. Plan optimization may also occur in treatment planning step 503, in which one or more plans for the planned treatment are optimized. That is, one or more beam geometries for implementing the planned treatment are determined and a dose distribution for each beam geometry is optimized. A physician responsible for the patient reviews the available plans and selects the best plan to be delivered to the patient.

In delivery of treatment plan step 504, the selected treatment plan is delivered to the patient on a suitable radiation therapy system via a suitable radiation therapy process, according to various embodiments. In the embodiments, a virtual portal image is generated and displayed to a user to facilitate verification of patient positioning and target localization. For example, in embodiments in which the selected treatment plan is for a breast cancer treatment, the virtual portal image can facilitate verification of flash distance and heart/lung sparing. One such embodiment is described below in conjunction with FIG. 6.

Figure 6:
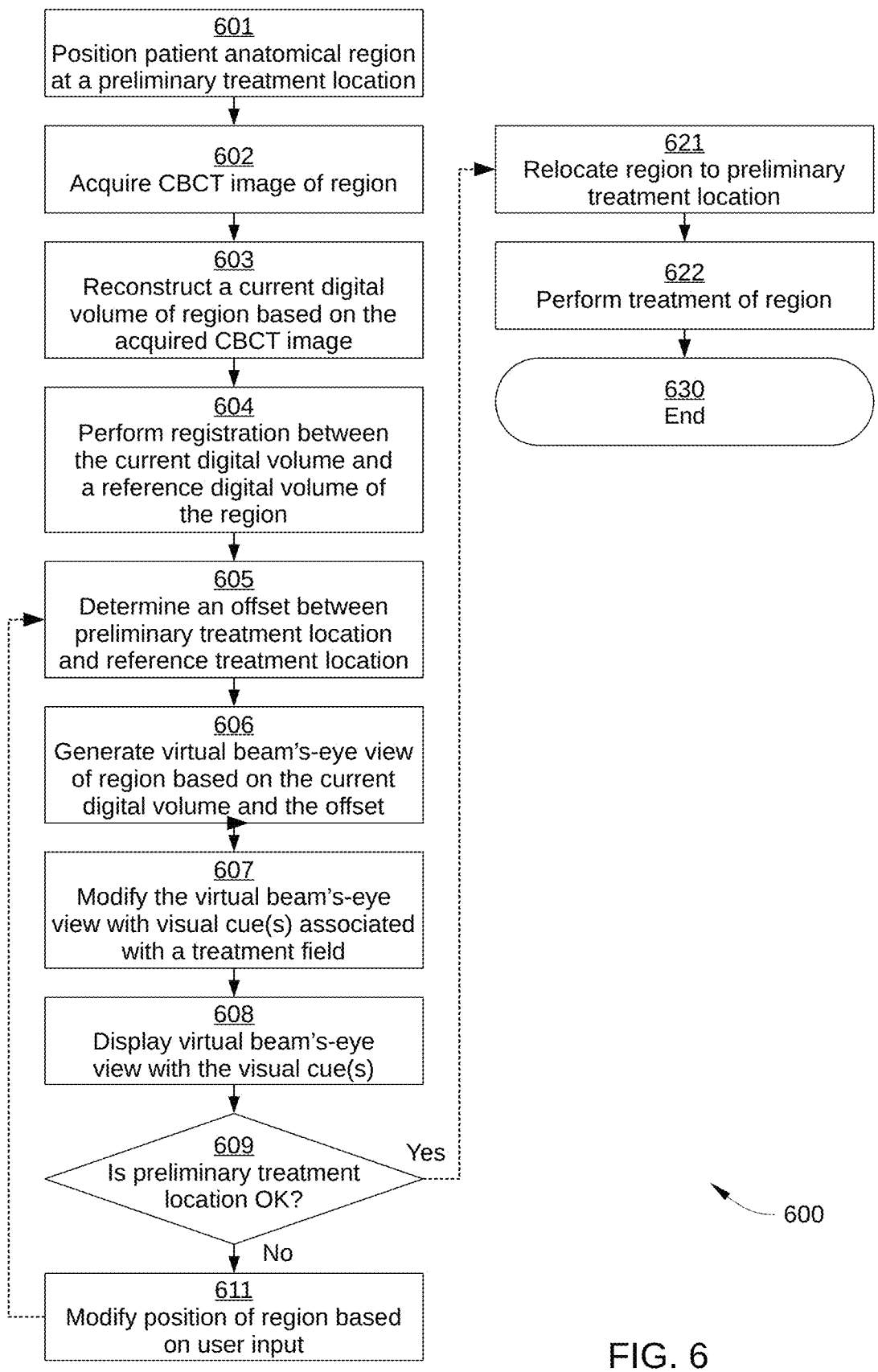
FIG. 6 sets forth a flowchart of a computer-implemented method for the setup and performance of a radiation therapy treatment plan in a radiation therapy system, according to one or more embodiments.

FIG. 6 sets forth a flowchart of a computer-implemented method 600 for the setup and performance of a radiation therapy treatment plan in a radiation therapy system, according to one or more embodiments. Computer-implemented method 600 may include one or more operations, functions, or actions as illustrated by one or more of blocks 601-630. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented method 600 is described in conjunction with RT system 100 and FIGS. 1-4, persons skilled in the art will understand that any suitably configured radiation therapy system is within the scope of the present embodiments.

Computer-implemented method 600 is generally performed in response to a particular patient arriving for a clinical session included in a radiation therapy treatment plan, for example to undergo a specific treatment fraction of the treatment plan. As noted previously, such a treatment plan is typically generated based on a reference image or reference digital volume of an anatomical region of the patient (such as digital volume 400) that includes a target volume (such as target volume 410). According to various embodiments, the digital volume is reconstructed based on imaging information obtained via a treatment planning scan, which can be performed using onboard imaging of RT system 100 or an independent CT scanning system. Prior to the herein-described treatment fraction, the patient is positioned on couch 107. In some instances, the patient is positioned in conjunction with prescribed immobilization, so that a suitable patient position is maintained during the treatment planning scan.

Computer-implemented method 600 begins at step 601, where a user positions an anatomical region of a patient at a preliminary treatment location. The anatomical region includes the target volume to undergo treatment, such as target volume 209. For example, based on external patient markings and a laser-based system associated with or included in RT system 100, the user can accurately position a patient close to the planned treatment position. However, accurately positioning a patient precisely at the planned treatment position requires further position verification and correction via time-of-treatment imaging, as described in step 602.

In step 602, RT system 110 generates time-of-treatment images. For example, in some embodiments, RT system 110 acquires, via a CBCT process, a set of 2D projection images of the anatomical region of the patient that includes target volume 209. In such embodiments, the set of 2D projection images can be combined, via a reconstruction process, to generate a three-dimensional digital volumetric image, as described in step 603.

In step 603, RT system 110 reconstructs a current digital volume of the anatomical region of the patient based on the 2D projection images or other treatment planning images generated in step 602. The current digital volume captures the current shape and precise location of the anatomical region of the patient and of target volume 209 disposed within the anatomical region. In some embodiments, the reconstruction is performed by one or more computing devices associated with image acquisition and treatment control computer 206 and/or remote control console 210. In some embodiments, the reconstructed volume 3D is a volumetric data set of the anatomical region. In some embodiments, a Feldkamp, Davis and Kress (FDK) reconstruction algorithm is employed to reconstruct the current digital volume, and in other embodiments, any other suitable reconstruction algorithm is employed.

In step 604, RT system 110 performs registration between the current digital volume reconstructed in step 603 and a reference digital volume of the anatomical region of the patient, such as the treatment planning image generated in acquisition of treatment planning CT step 502 in FIG. 5. For example, in some embodiments, a deformable image registration process is automatically performed by RT system 110. Alternatively, in some embodiments, RT system 110 uses any other technically feasible image registration and fusion process. Alternatively, in some embodiments, a user of RT system 110 performs a manual, landmark □based registration or matching process to perform registration between the current digital volume and the reference digital volume.

In step 605, RT system 110 determines an offset between the current preliminary treatment location and a reference treatment location. For example, in some embodiments, the offset is based on a transformation determined from the image registration of step 604. Thus, in such embodiments, the offset is between the current position (at time of treatment) of the anatomical region and target volume 209, and the planned treatment position, which is the assumed position of the anatomical region and target volume 209. It is noted that the planned treatment for target volume 209 is based on the anatomical region that includes target volume 209 being located precisely at the planned treatment position. Therefore, in such embodiments, the offset determined in step 605 approximates how far the current position of target volume 209 is from the planned treatment position.

Alternatively or additionally, in some embodiments, the offset is based on user inputs indicating that the patient should be relocated a specified quantity and distance. In such embodiments, the user input may be received in step 609, for example in response to a user reviewing a virtual beam's-eye view of the anatomical region that includes target volume 209. Thus, in such embodiments, the offset is between the current preliminary treatment location of the anatomical region and a new preliminary treatment location that corresponds to the location indicated by the user input received in step 609. In such embodiments, the new preliminary treatment location is associated with improved flash distance and/or OAR sparing, as described below.

In step 606, RT system 110 generates a virtual beam's-eye view of the anatomical region, where the virtual beam's eye view is directed along a path of treatment beam 230. Generally, the visual information included in the beam's-eye view is based on volumetric image data of the current digital volume generated in step 603 and on the offset determined in step 605. This is because the actual path of treatment beam 230 relative to target volume 209 varies as a function of the offset between the planned treatment position and the current location of target volume 209. Thus, when there is a significant offset between the current preliminary treatment location and the reference treatment location, the actual path of treatment beam 230 is less than ideal, and follows a different path than the planned path. As a result, the treatment field associated with treatment beam 230 may have an insufficient flash distance and/or OAR sparing.

Generally, the virtual beam's-eye view is generated to appear to be taken from the point of view of the source of treatment beam 230 for a specific beam angle of treatment beam 230 that is programmed to occur during the present treatment of target volume 209. In some embodiments, multiple virtual beam's-eye views of the anatomical region are generated in step 606, such as when multiple beam angles of treatment beam 230 are programmed to occur during the present treatment of target volume 209.

In some embodiments, the virtual beam's-eye view of the anatomical region is a digitally reconstructed radiograph (DRR). In such embodiments, the virtual beam's-eye view of the anatomical region is acquired through perspective projection of the digital volume along a path of treatment beam 230 for the target volume 209. Any suitable DRR generation algorithm or other software for processing the current digital volume can be employed in step 606 to generate the virtual beam's-eye view. Further, in some embodiments, the one or more virtual beam's-eye views generated in step 606 simulate the appearance of an MV portal image. In such embodiments, the virtual beam's-eye-view image(s) appear substantially similar to a traditionally generated MV portal image, which can significantly increase the confidence and speed of a user when viewing such image(s) to verify patient positioning and target localization. Generally, to generate the perspective projection of a DRR, a projection algorithm uses ray tracing through a CT data set, such as the volumetric image data of the current digital volume generated in step 603. In the ray tracing, each resulting output pixel is traced forward from the X-ray source point through the CT volume onto the imaging plane (such as X-ray imager 207), where each ray uses a function to sample the values along the ray and cumulate the values in order to calculate the final output pixel value. Because the absorption rate of the material depends on the energy spectrum of the X-ray, the resulting DRR can resemble an actual radiograph taken at the spectrum that corresponds to an MV portal image. For example, in one embodiment, a spectrum corresponding to a 6 MeV therapy beam is employed when generating the beam's-eye view of the anatomical region instead of a spectrum that corresponds to a 100 keV beam used for standard X-ray imaging.

In step 607, RT system 110 modifies the virtual beam's-eye view(s) generated in step 606 with one or more visual cues associated with a treatment field of treatment beam 230. For example, in some embodiments, RT system 110 modifies a virtual beam's-eye view with a field outline of the treatment field associated with treatment beam 230, a radiation field isocenter indicator for the treatment field associated with treatment beam 230, a graticule, or some combination thereof. An embodiment of one such virtual beam's-eye view is described below in conjunction with FIG. 7.

Figure 7:
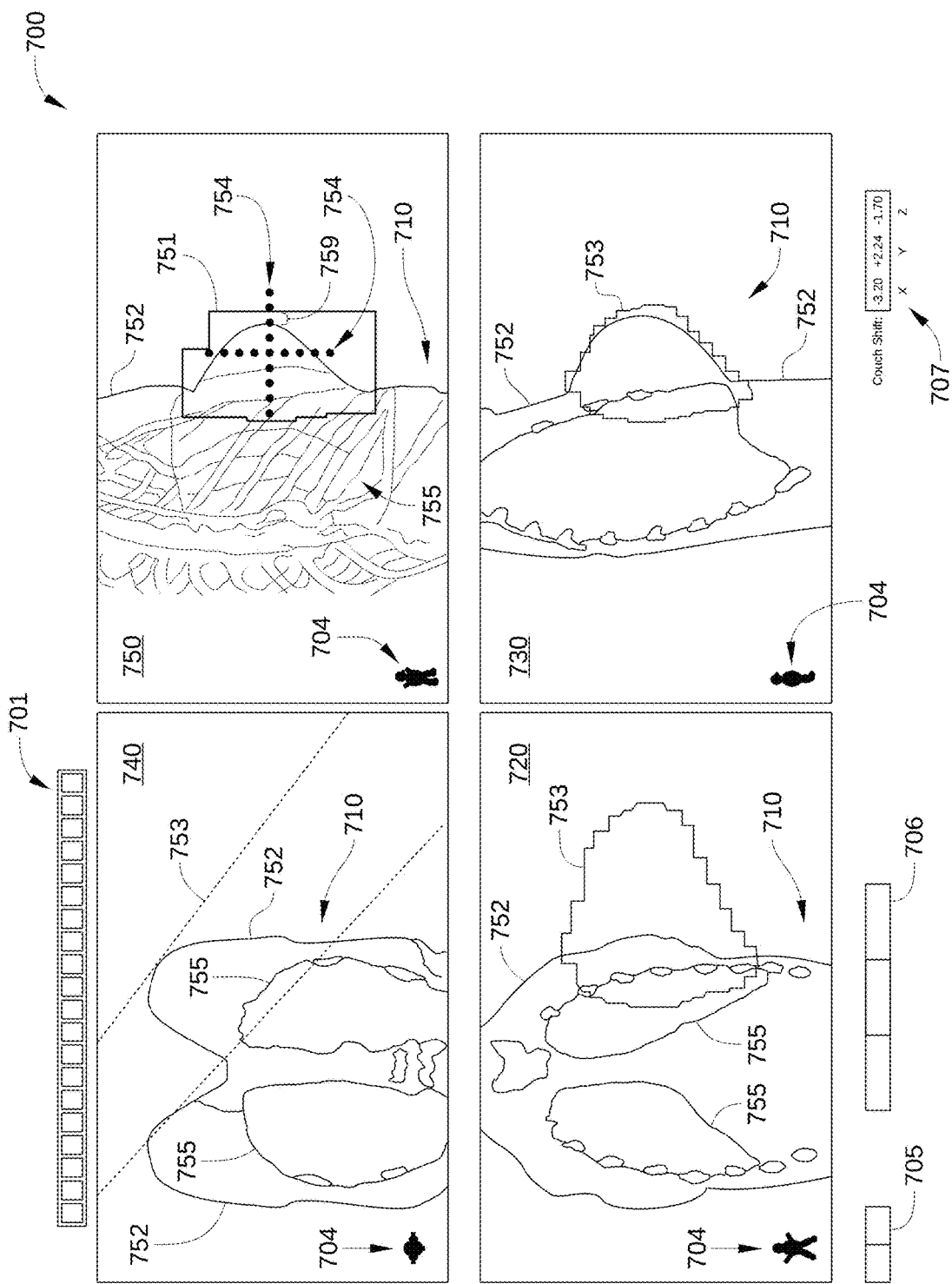
FIG. 7 schematically illustrates a graphical user interface that facilitates verification of patient positioning and target localization with respect to a treatment plan, according to various embodiments.

FIG. 7 schematically illustrates a graphical user interface (GUI) 700 that facilitates verification of patient positioning and target localization with respect to a treatment plan, according to various embodiments. For example, in embodiments in which the treatment plan is for a breast cancer treatment, the virtual portal image can facilitate verification of flash distance and heart/lung sparing. Further, GUI 700 facilitates calculation of shift parameters automatically positioning couch 107 when there is a significant offset between a preliminary treatment location and a reference treatment location associated with the treatment plan.

As shown, GUI 700 includes input elements 701, patient orientation indicators 704, a taskbar 705, multiple action buttons 706, and a couch shift indicator 707. Input elements 701 include graphical buttons and/or other input mechanisms for user interactions, such as imaging tools that enable a radiation therapist to change the display of the images in various ways. For example, one such tool may apply filters that improve image quality and facilitate matching of images and/or verification of matched images. Another such tool can be a blending slider for comparing the position of patient anatomy in a reference image and in an acquired image. Patient orientation indicators 704 indicate the anatomical position and relative relationship of an image to anatomical nomenclature in each view window of GUI 700. Taskbar 705 provides options for selecting the imaging mode and a particular matching technique to be employed by RT system 100 and/or by the radiation therapist. The multiple action buttons 706 variously apply a calculated shift to the position of couch 107, enable resetting of changes, perform adjustments to the match, cancel the current match, and/or reacquire a setup image, among other functions. Couch shift indicator 707 displays the distance each couch axis should move to correctly position the patient for treatment. In some embodiments, the values displayed by couch shift indicator 707 can be based at least in part on the offset determined in step 605 of computer-implemented method 600. In addition, in some embodiments, when a radiation therapist or other user of RT system 100 adjusts the matching between a reference image and a time-of-treatment setup image, the couch shift values displayed by shift indicator 707 are updated. For example, a radiation therapist or other user of RT system 100 may input adjustments to couch shift indicator 707 that improve a flash distance and/or OAR sparing.

GUI 700 further includes a coronal (or frontal) plane view 720, a sagittal plane view 730, an axial plane view 740, and a virtual beam's-eye-view (BEV) window 750. GUI 700 allows a user to visually compare and/or match reference images and time-of-treatment images via coronal plane view 720, sagittal plane view 730, axial plane view 740, and virtual BEV window 750. That is, in the four above-described views, a reference image, such as an image of patient anatomy based on the treatment planning image, and a time-of-treatment setup image, based on the current digital volume, can be compared.

Coronal plane view 720 enables the display and matching of reference 2D images and time-of-treatment 2D images in a coronal view (i.e., a view along an axis perpendicular to the coronal plane), sagittal plane view 730 enables the display and matching of reference 2D images and time-of-treatment 2D images in a sagittal view, and axial plane view 740 enables the display and matching of reference 2D images and time-of-treatment 2D images in an axial view. Furthermore, virtual BEV window 750 enables the display and matching of reference 2D views and time-of-treatment 2D views in a beam's-eye view (i.e., a view along an axis parallel to a specific path of the planned treatment beam).

For the reference 2D views and the time-of-treatment 2D views displayed in coronal plane view 720, sagittal plane view 730, or axial plane view 740, the image plane is considered the physical plane corresponding to the location of the 2D virtual slice. In some embodiments, for virtual BEV images displayed by virtual BEV window 750, the image plane is considered the projection plane of the virtual BEV image.

Virtual BEV window 750 is configured to display reference 2D BEV views and time-of-treatment 2D BEV views for any beam angle of the planned treatment beam. By contrast, each of coronal plane view 720, sagittal plane view 730, and axial plane view 740, is configured to display reference 2D images and time-of-treatment 2D images from a single fixed point of view (or viewing angle). Thus, the image plane for each reference 2D image or time-of-treatment 2D image displayed in, for instance, sagittal plane view 730 is parallel with the image plane of any other reference 2D view or time-of-treatment 2D view displayed in sagittal plane view 730, while the image plane for each 2D BEV view displayed by virtual BEV window 750 is generally not parallel with the image plane of other 2D BEV images displayed by virtual BEV window 750.

Each of coronal plane view 720, sagittal plane view 730, axial plane view 740, and virtual BEV window 750 displays a portion of patient anatomy 710. In coronal plane view 720, sagittal plane view 730, axial plane view 740, patient anatomy 710 is displayed as a 2D image of a virtual slice through patient anatomy 710. By contrast, in embodiments in which virtual BEV window 750 displays a projected DRR image, patient anatomy is shown as a virtual projected view in virtual BEV window 750, simulating a conventional X-ray image. In such embodiments, the image displayed in virtual BEV window 750 has an image plane that is perpendicular to a path of a particular planned treatment beam that passes through the image plane.

In some embodiments, some or all of coronal plane view 720, sagittal plane view 730, axial plane view 740, and virtual BEV window 750 can be selected to display a time-of-treatment 2D image of patient anatomy 710, a reference 2D image of patient anatomy, a time-of-treatment 2D image superimposed on a reference 2D image, or a blended view of patient anatomy 710, in which a radiation therapist can simultaneously view a reference 2D image and a time-of-treatment 2D image. For clarity, in the embodiment illustrated in FIG. 7, GUI 700 displays time-of-treatment 2D images of patient anatomy 710 in coronal plane view 720, sagittal plane view 730, axial plane view 740, and virtual BEV window 750.

Figure 8A:
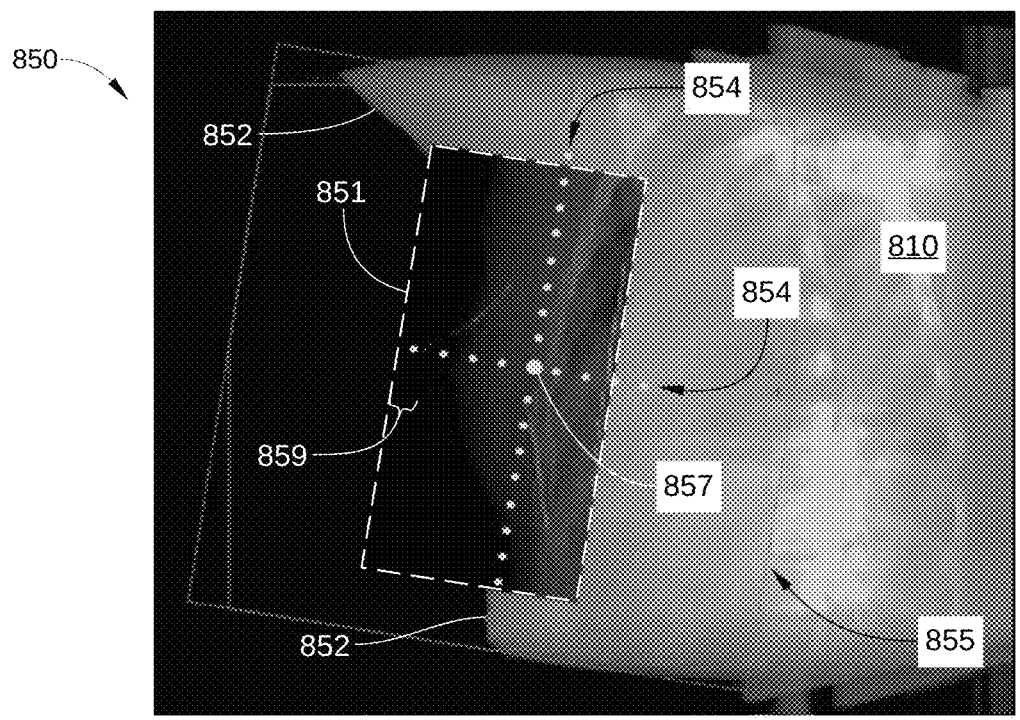
FIG. 8A is a virtual beam's-eye view of a portion of patient anatomy, according to various embodiments.
Figure 8B:
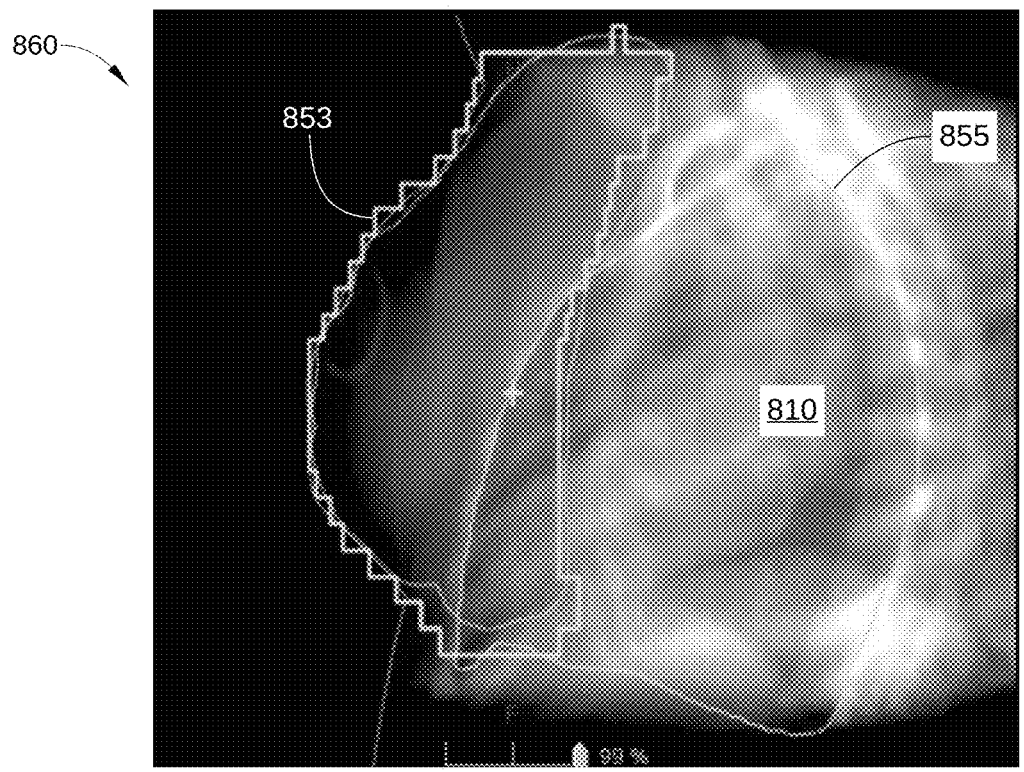
FIG. 8B is a conventional virtual beam's-eye view of a portion of patient anatomy.

In some embodiments virtual BEV window 750 displays a virtual beam's-eye view of patient anatomy 710 that simulates or visually mimics a traditionally acquired MV portal image. One such embodiment is described below in conjunction with FIGS. 8A and 8B. FIG. 8A is a virtual beam's-eye view 850 of a portion of patient anatomy 810, according to various embodiments, and FIG. 8B is a conventional virtual beam's-eye view 860 of the same portion of patient anatomy 810. Virtual beam's-eye view 850 and conventional virtual beam's-eye view 860 each depict a view along an axis parallel to a specific path of the planned treatment beam. Further, virtual beam's-eye view 850 and conventional virtual beam's-eye view 860 are each DRRs that are generated based on the current digital volume reconstructed in step 603 of FIG. 6. However, in the embodiment illustrated in FIG. 8A, image processing is applied to the perspective projection of the current digital volume, such that virtual beam's-eye view 850 visually mimics the appearance of a traditionally acquired MV portal image.

In some embodiments, virtual beam's-eye view 850 includes a field outline 851, a graticule 854 or other graduated position indicator, and/or an indicator 857 of a radiation field isocenter. By contrast, conventional virtual beam's-eye view 860 includes extents 853 of the planned treatment beam. Field outline 851 visually indicates an extent of the planned treatment beam relative to patient anatomy 810 while located at the current preliminary treatment location. Because field outline 851 is displayed in a beam's-eye view that shows the farthest extent of the surface 852 of skin relative to the planned treatment beam, a user can readily determine a minimum flash distance 859 associated with the planned treatment beam while the patient is located at the current preliminary treatment location. Graticule 854 is a graduated position indicator that includes uniformly spaced markers, dots, and/or lines that are separated by a specified distance, and therefore precisely indicates various locations within field outline 851. For example, in some embodiments, the spaced markers of graticule 854 are separated from adjacent spaced markers by 1 cm. Thus, graticule 854 enables a user viewing virtual beam's-eye view 850 to determine a distance within patient anatomy 810 associated with flash distance 859 and/or sparing of an OAR, such as lung 855. In some embodiments, indicator 857 depicts the position relative to patient anatomy 810 of a radiation field isocenter associated with the planned treatment beam.

Returning to FIG. 7, according to various embodiments, virtual BEV window 750 can be used to verify flash distance 759 for a specific beam angle of the treatment beam that is programmed to occur during treatment. Thus, using virtual BEV window 750, the user can verify that, at the specific beam angle, the treatment beam extends past surface 752 of the skin by at least a predetermined distance (e.g., 1 cm, 2 cm, etc.). In addition, in various embodiments, virtual BEV window 750 can be used to determine sufficient sparing of one or more OARs, such as the heart or lungs 755. To these ends, in some embodiments, GUI 700 is configured to display a field outline 751 of the planned treatment beam relative to the anatomy of the patient while at the current preliminary treatment location. Additionally or alternatively, in some embodiments, GUI 700 is configured to display a graticule 754 or other graduated position indicator. In such embodiments, graticule 754 includes uniformly spaced markers, dots, and/or lines that are separated by a specified distance, and therefore precisely indicate various locations within field outline 751. In addition, in the embodiment illustrated in FIG. 7, extents 753 of the planned treatment beam are displayed in each of coronal plane view 720, sagittal plane view 730, and axial plane view 740.

It is noted that verifying flash distance 759 and/or OAR sparing when only viewing extents 753 (in coronal plane view 720, sagittal plane view 730, and/or axial plane view 740) can be unreliable and/or time-consuming compared to viewing field outline 751 in virtual BEV window 750. This is especially true for a radiation therapist, physician, or other user of RT system 100 who is accustomed to a beam's-eye view of patient anatomy 710 having the appearance and layout of a traditional portal image, as shown in FIG. 8A. For example, when using axial plane view 740 and extents 753 to verify flash distance 759 and/or sparing of lung 755, a user of RT system 100 visually reviews each axial view available in axial plane view 740. Specifically, to confirm that at least a minimum allowable flash distance 759 is maintained and/or a maximum allowable overlap of lung 755 is not exceeded, the user cycles through all axial view slices of patient anatomy 710 and visually determines the location of extents 753 of the planned treatment beam relative to surface 752 of patient skin and/or any OARs. For example, the user may mouse scroll, or actuate a GUI element such as a slider, to cycle through the many axial view slices of patient anatomy 710 that are available in axial plane view 740. Thus, a user who is accustomed to the appearance and layout of a traditional portal image may be hesitant and/or unable to verify flash distance 759 and/or a maximum allowable overlap of lung 755 via review of axial plane view 740.

By contrast, in virtual BEV window 750, surface 752 of patient skin relative to field outline 751 of the planned treatment beam is readily determined visually for any particular angle of the planned treatment by reviewing a single beam's-eye view of patient anatomy 710 in virtual BEV window 750. Further, without specialized training, many users who are accustomed to traditionally generated BEVs are generally less comfortable using a virtual beam's-eye view showing individual 2D slices of patient anatomy.

Returning to FIG. 6, in step 608 RT system 100 displays a virtual beam's eye view of patient anatomy, for example via virtual BEV window 750 shown in FIG. 7. In some embodiments, virtual BEV window 750 includes field outline 751, graticule 754, and/or an indicator 857 depicting the position of a radiation field isocenter.

In step 609, RT system 100 determines whether the current preliminary treatment location is suitable for treatment to begin. In some embodiments, the determination is made in response to a user input. For example, in some instances, the user input confirms the current preliminary treatment location is suitable for treatment. In other instances, the user input indicates that the patient should be relocated a specified quantity and distance, for example to better align the location of the patient with the planned treatment position. For example, in such instances, a user may enter one or more coordinate shifts via a GUI of RT system 100 to compensate for an inadequate flash distance and/or OAR sparing for one or more specific beam angles of the treatment beam. It is noted that the offset determined in step 605 between the preliminary treatment location and the reference treatment location may not be the only cause of the inadequate flash distance and/or OAR sparing. For example, changes in the size and/or shape of organs in the anatomical region that includes the target volume can also reduce flash distance and/or OAR sparing.

When RT system 100 determines that the current preliminary treatment location is suitable for treatment to begin, computer-implemented method 600 proceeds to step 621; when RT system 100 determines that the current preliminary treatment location is not suitable for treatment to begin, computer-implemented method 600 proceeds to step 611.

In step 611, RT system 100 modifies the position of the anatomical region and target volume based on the user input indicating that the patient should be relocated a specified quantity and distance. For example, in some embodiments, the input includes one or more values for shift parameters used to automatically position couch 107. Computer-implemented method 600 then returns to step 605 for another iteration of steps 605-609.

In step 621, RT system 100 relocates the anatomical region and target volume 209 to the final treatment location, based on the offsets determined in each iteration of step 605. For example, in some embodiments, RT system 100 repositions couch 107 to the final treatment location based on such offsets, where the final treatment location corresponds to the last preliminary treatment location determined in step 609.

In step 622, RT system 100 performs treatment of target volume 209. In some embodiments, RT system 110 receives a user input to initiate treatment and performs treatment while the patient is disposed at the final treatment location. For example, in some embodiments, RT system 110 directs a treatment beam to target volume 209 in accordance with the treatment plan associated with target volume 209.

Implementation of computer-implemented method 600 as described above enables fast and accurate visual confirmation that a patient is correctly positioned relative to a planned treatment isocenter via a virtual beam's-eye view of patient anatomy that closely approximates a traditionally acquired portal image. In addition, the above-described virtual beam's-eye view is generated without the additional dosing associated with a traditionally acquired portal image. Further, because iterations of steps 605-611 can be performed in essentially real time by a conventional radiation therapy system that includes on-board imaging, a user can quickly determine how to reposition a patient, to improve patient positioning and/or target localization. Even when multiple iterations of steps 605-611 are required to determine a suitable final treatment position, the user can quickly improve patient positioning and/or target localization after time-of-treatment imaging and prior to treatment.

Exemplary Computing Device

Figure 9:
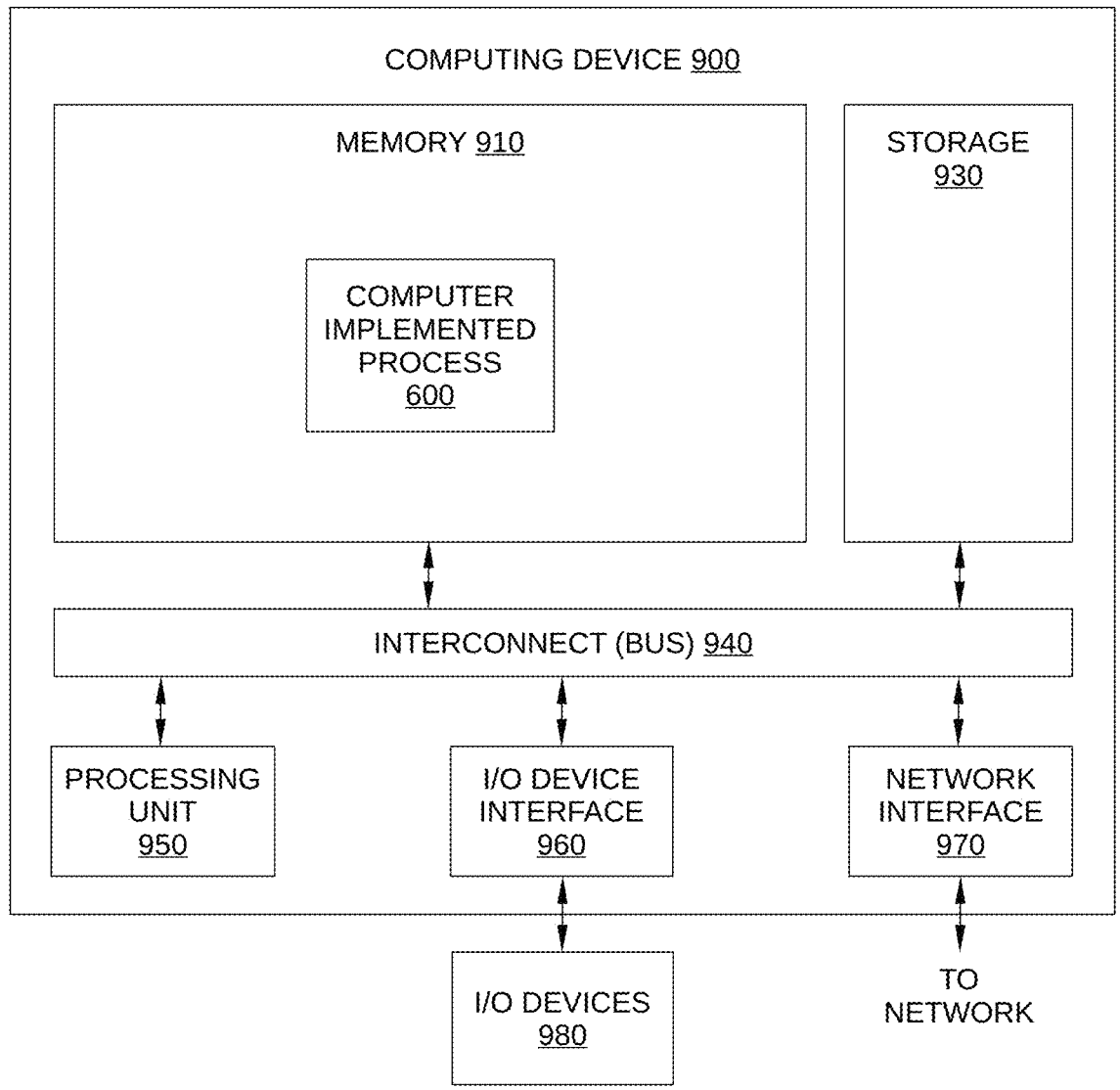
FIG. 9 is an illustration of a computing device configured to perform various embodiments of the present disclosure.

FIG. 9 is an illustration of computing device 900 configured to perform various embodiments of the present disclosure. Thus, in some embodiments, computing device 900 is implemented as or associated with image acquisition and treatment control computer 106 and/or remote control console 110. Computing device 900 may be a desktop computer, a laptop computer, a smart phone, or any other type of computing device suitable for practicing one or more embodiments of the present disclosure. In operation, computing device 900 is configured to execute instructions associated with computer-implemented method 600 as described herein. It is noted that the computing device described herein is illustrative and that any other technically feasible configurations fall within the scope of the present disclosure.

As shown, computing device 900 includes, without limitation, an interconnect (bus) 940 that connects a processing unit 950, an input/output (I/O) device interface 960 coupled to input/output (I/O) devices 980, memory 910, a storage 930, and a network interface 970. Processing unit 950 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 950 may be any technically feasible hardware unit capable of processing data and/or executing software applications, including computer-implemented method 600.

I/O devices 980 may include devices capable of providing input, such as a keyboard, a mouse, a touch-sensitive screen, and so forth, as well as devices capable of providing output, such as a display device and the like. Additionally, I/O devices 980 may include devices capable of both receiving input and providing output, such as a touchscreen, a universal serial bus (USB) port, and so forth. I/O devices 980 may be configured to receive various types of input from an end-user of computing device 900, and to also provide various types of output to the end-user of computing device 900, such as displayed digital images or digital videos. In some embodiments, one or more of I/O devices 980 are configured to couple computing device 900 to a network.

Memory 910 may include a random access memory (RAM) module, a flash memory unit, or any other type of memory unit or combination thereof. Processing unit 950, I/O device interface 960, and network interface 970 are configured to read data from and write data to memory 910. Memory 910 includes various software programs that can be executed by processor 950 and application data associated with said software programs, including computer-implemented method 600.

Exemplary Computer Program Product

Figure 10:
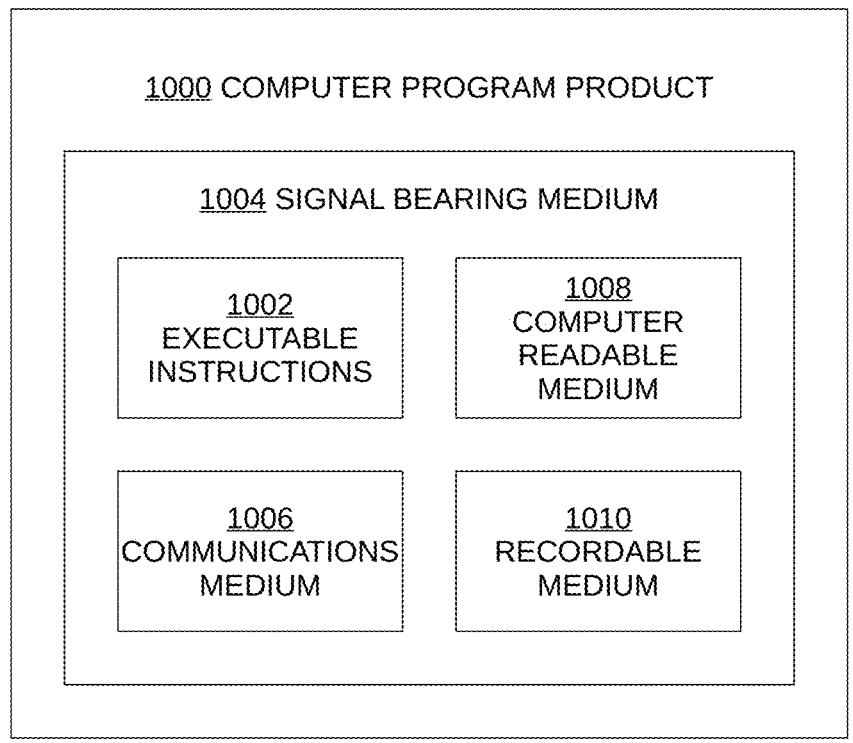
FIG. 10 is a block diagram of an illustrative embodiment of a computer program product for implementing one or more embodiments of the present disclosure.

FIG. 10 is a block diagram of an illustrative embodiment of a computer program product 1000 for implementing a method of performing radiation therapy on a target volume within an anatomical region of a patient, according to one or more embodiments of the present disclosure. Computer program product 1000 may include a signal bearing medium 1004. Signal bearing medium 1004 may include one or more sets of executable instructions 1002 that, when executed by, for example, a processor of a computing device, may provide at least the functionality described above with respect to FIGS. 1-8.

In some implementations, signal bearing medium 1004 may encompass a non-transitory computer readable medium 1008, such as, but not limited to, a hard disk drive, a Compact Disc (CD), a Digital Video Disk (DVD), a digital tape, memory, etc. In some implementations, signal bearing medium 1004 may encompass a recordable medium 1010, such as, but not limited to, memory, read/write (R/W) CDs, R/W DVDs, etc. In some implementations, signal bearing medium 1004 may encompass a communications medium 1006, such as, but not limited to, a digital and/or an analog communication medium (e.g., a fiber optic cable, a waveguide, a wired communications link, a wireless communication link, etc.). Computer program product 1000 may be recorded on non-transitory computer readable medium 1008 or another similar recordable medium 1010.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A computer-implemented method of performing radiation therapy on a target volume within an anatomical region of a patient, the method comprising:
   acquiring a cone-beam computed tomography (CBCT) image of the anatomical region while the anatomical region is positioned in a first preliminary treatment location;
   reconstructing a current digital volume of the anatomical region based on the CBCT image of the anatomical region;
   generating a first beam's-eye-view of the anatomical region based on the current digital volume and an offset between the first preliminary treatment location and a reference treatment location;
   modifying the first beam's-eye-view of the anatomical region with one or more visual cues associated with a treatment field for the target volume; and
   displaying the first beam's-eye-view with the one or more visual cues.

2. The computer-implemented method of claim 1, further comprising, after displaying the first beam's-eye-view with the one or more visual cues:
   receiving a user input indicating a position change of the anatomical region from the first preliminary treatment location to a second preliminary treatment location; and
   in response, generating a second beam's-eye-view of the anatomical region based on the current digital volume and the second preliminary treatment location.

3. The computer-implemented method of claim 1, further comprising, after displaying the first beam's-eye-view with the one or more visual cues:
   receiving a user input indicating acceptance of the first preliminary treatment location; and
   in response, delivering the treatment field to the target volume while the anatomical region is positioned in the first preliminary treatment location.

4. The computer-implemented method of claim 1, further comprising determining the offset between the first preliminary treatment location and the reference treatment location by matching the current digital volume of the anatomical region to a reference digital volume of the anatomical region.

5. The computer-implemented method of claim 1, wherein the one or more visual cues associated with the treatment field comprise at least one of a field outline of the treatment field or a graticule.

6. The computer-implemented method of claim 5, wherein the graticule includes a radiation field isocenter indicator.

7. The computer-implemented method of claim 5, wherein field outline indicates a flash distance.

8. The computer-implemented method of claim 1, wherein the reference treatment location is based on a reference digital volume of the anatomical region.

9. The computer-implemented method of claim 8, wherein the reference digital volume comprises a treatment planning image of the anatomical region.

10. The computer-implemented method of claim 1, wherein generating the first beam's-eye view of the anatomical region based on the current digital volume comprises generating a digitally reconstructed radiograph of the anatomical region.

11. The computer-implemented method of claim 1, wherein generating the first beam's-eye view of the anatomical region based on the current digital volume comprises generating a digitally reconstructed radiograph through perspective projection of the digital volume along a path of a treatment beam for the target volume.

12. The computer-implemented method of claim 1, wherein generating the first beam's-eye view of the anatomical region comprises simulating a megavolt portal image acquired through perspective projection of the digital volume along a path of a treatment beam for the target volume.

13. A radiation treatment system comprising:
   an imaging X-ray source configured to rotate about an isocenter of the radiation treatment system and direct imaging X-rays to a target region that includes a target volume; and
   a processor configured to perform the steps of:
      acquiring a cone-beam computed tomography (CBCT) image of the target region with the imaging X-ray source while the target region is positioned in a first preliminary treatment location;
      reconstructing a current digital volume of the target region based on the CBCT image of the target region;
      generating a first beam's-eye-view of the target region based on the current digital volume and an offset between the first preliminary treatment location and a reference treatment location;
      modifying the first beam's-eye-view of the target region with one or more visual cues associated with a treatment field for the target volume; and
      displaying the first beam's-eye-view with the one or more visual cues.

14. The radiation treatment system of claim 13, wherein the steps further comprise, after displaying the first beam's-eye-view with the one or more visual cues:
   receiving a user input indicating a position change of the target region from the first preliminary treatment location to a second preliminary treatment location; and
   in response, generating a second beam's-eye-view of the target region based on the current digital volume and the second preliminary treatment location.

15. The radiation treatment system of claim 13, wherein the steps further comprise, after displaying the first beam's-eye-view with the one or more visual cues:
   receiving a user input indicating acceptance of the first preliminary treatment location; and
   in response, delivering the treatment field to the target volume while the target region is positioned in the first preliminary treatment location.

16. The radiation treatment system of claim 13, wherein the steps further comprise determining the offset between the first preliminary treatment location and the reference treatment location by matching the current digital volume of the target region to a reference digital volume of the target region.

17. The radiation treatment system of claim 13, wherein the one or more visual cues associated with the treatment field comprise at least one of a field outline of the treatment field or a graticule.

18. The radiation treatment system of claim 17, wherein the graticule includes a radiation field isocenter indicator.

19. The radiation treatment system of claim 17, wherein field outline indicates a flash distance.

20. The radiation treatment system of claim 13, wherein the reference treatment location is based on a reference digital volume of the target region.

* * * * *